United States Patent [19]

Nicholson et al.

[11] Patent Number: 6,103,513
[45] Date of Patent: Aug. 15, 2000

[54] INTERLEUKIN-1β CONVERTING ENZYME-RELATED CYSTEINE PROTEINASE II (ICE$_{REL}$-II)

[75] Inventors: Donald W. Nicholson, Montreal; Ambereen Ali, Pierrefonds; Neil A. Munday, Guelph; John P. Vaillancourt, Pierrefonds, all of Canada

[73] Assignee: Merck Frosst Canada & Co., Province of Quebec, Canada

[21] Appl. No.: 08/721,986

[22] PCT Filed: Apr. 4, 1995

[86] PCT No.: PCT/CA95/00188

§ 371 Date: Feb. 10, 1997

§ 102(e) Date: Feb. 10, 1997

[87] PCT Pub. No.: WO95/27793

PCT Pub. Date: Oct. 19, 1995

Related U.S. Application Data

[63] Continuation of application No. 08/225,487, Apr. 8, 1994.

[51] Int. Cl.[7] ............... C12N 9/50; C12N 9/64; C07H 21/04

[52] U.S. Cl. ............ 435/219; 435/226; 435/212; 435/23; 530/350; 530/351; 536/23.2; 536/23.5

[58] Field of Search ............ 435/219, 226, 435/212, 23; 530/350, 351; 536/23.2, 23.5

[56] References Cited

U.S. PATENT DOCUMENTS 5,416,013  5/1995  Black et al. .................. 435/226

OTHER PUBLICATIONS

Cerretti et al., *Science*, vol. 256, Apr. 3, 1992, pp. 97–100.

*Primary Examiner*—Carla J. Myers
*Attorney, Agent, or Firm*—Joseph A. Coppola; Jack L. Tribble

[57] ABSTRACT

A complementary DNA (cDNA) encoding full length form of ICE$_{rel}$-II is identified, sequenced and isolated. The cDNA is cloned into expression vectors for expression in recombinant hosts. The cDNA is useful to produce recombinant full length ICE$_{rel}$-II. The cDNA and the recombinant ICE$_{rel}$-II protein derived therefrom are useful in diagnostic kits, laboratory reagents and assays. The cDNA and the recombinant ICE$_{rel}$-II protein may be used to identify compounds that affect ICE$_{rel}$-II function, inflammation and cell apoptosis. ICE$_{rel}$-II function, inflammation and cell apoptosis may also be modulated by ICE$_{rel}$-II antisense or gene therapy.

2 Claims, 6 Drawing Sheets

```
    TTTCCAACGCTGTAAAAAAGGACAGAGGCTGTTCCCTATGGCAGAAGGCAACCACAGAAA
  1 ─────────┼─────────┼─────────┼─────────┼─────────┼─────────┼ 60
    AAAGGTTGCGACATTTTTTCCTGTCTCCGACAAGGGATACCGTCTTCCGTTGGTGTCTTT
                                            MetAlaGluGlyAsnHisArgLy

AAAGCCACTTAAGGTGTTGGAATCCCTGGGCAAAGATTTCCTCACTGGTGTTTTGGATAA
 61 ─────────┼─────────┼─────────┼─────────┼─────────┼─────────┼ 120
    TTTCGGTGAATTCCACAACCTTAGGGACCCGTTTCTAAAGGAGTGACCACAAAACCTATT
    sLysProLeuLysValLeuGluSerLeuGlyLysAspPheLeuThrGlyValLeuAspAs

CTTGGTGGAACAAAATGTACTGAACTGGAAGGAAGAGGAAAAAAAGAAATATTACGATGC
121 ─────────┼─────────┼─────────┼─────────┼─────────┼─────────┼ 180
    GAACCACCTTGTTTTACATGACTTGACCTTCCTTCTCCTTTTTTTCTTTATAATGCTACG
    nLeuValGluGlnAsnValLeuAsnTrpLysGluGluGluLysLysLysTyrTyrAspAl

TAAAACTGAAGACAAAGTTCGGGTCATGGCAGACTCTATGCAAGAGAAGCAACGTATGGC
181 ─────────┼─────────┼─────────┼─────────┼─────────┼─────────┼ 240
    ATTTTGACTTCTGTTTCAAGCCCAGTACCGTCTGAGATACGTTCTCTTCGTTGCATACCG
    aLysThrGluAspLysValArgValMetAlaAspSerMetGlnGluLysGlnArgMetAl

AGGACAAATGCTTCTTCAAACCTTTTTTAACATAGACCAAATATCCCCCAATAAAAAAGC
241 ─────────┼─────────┼─────────┼─────────┼─────────┼─────────┼ 300
    TCCTGTTTACGAAGAAGTTTGGAAAAAATTGTATCTGGTTTATAGGGGGTTATTTTTTCG
    aGlyGlnMetLeuLeuGlnThrPhePheAsnIleAspGlnIleSerProAsnLysLysAl

TCATCCGAATATGGAGGCTGGACCACCTGAGTCAGGAGAATCTACAGATGCCCTCAAGCT
301 ─────────┼─────────┼─────────┼─────────┼─────────┼─────────┼ 360
    AGTAGGCTTATACCTCCGACCTGGTGGACTCAGTCCTCTTAGATGTCTACGGGAGTTCGA
    aHisProAsnMetGluAlaGlyProProGluSerGlyGluSerThrAspAlaLeuLysLe

TTGTCCTCATGAAGAATTCCTGAGACTATGTAAAGAAAGAGCTGAAGAGATCTATCCAAT
361 ─────────┼─────────┼─────────┼─────────┼─────────┼─────────┼ 420
    AACAGGAGTACTTCTTAAGGACTCTGATACATTTCTTTCTCGACTTCTCTAGATAGGTTA
    uCysProHisGluGluPheLeuArgLeuCysLysGluArgAlaGluGluIleTyrProIl

AAAGGAGAGAAACAACCGCACACGCCTGGCTCTCATCATATGCAATACAGAGTTTGACCA
421 ─────────┼─────────┼─────────┼─────────┼─────────┼─────────┼ 480
    TTTCCTCTCTTTGTTGGCGTGTGCGGACCGAGAGTAGTATACGTTATGTCTCAAACTGGT
    eLysGluArgAsnAsnArgThrArgLeuAlaLeuIleIleCysAsnThrGluPheAspHi
```

FIG.1A

```
       TCTGCCTCCGAGGAATGGAGCTGACTTTGACATCACAGGGATGAAGGAGCTACTTGAGGG
481    ------+------+------+------+------+------+  540
       AGACGGAGGCTCCTTACCTCGACTGAAACTGTAGTGTCCCTACTTCCTCGATGAACTCCC
       sLeuProProArgAsnGlyAlaAspPheAspIleThrGlyMetLysGluLeuLeuGluGl

TCTGGACTATAGTGTAGATGTAGAAGAGAATCTGACAGCCAGGGATATGGAGTCAGCGCT
541    ------+------+------+------+------+------+  600
       AGACCTGATATCACATCTACATCTTCTCTTAGACTGTCGGTCCCTATACCTCAGTCGCGA
       yLeuAspTyrSerValAspValGluGluAsnLeuThrAlaArgAspMetGluSerAlaLe

GAGGGCATTTGCTACCAGACCAGAGCACAAGTCCTCTGACAGCACATTCTTGGTACTCAT
601    ------+------+------+------+------+------+  660
       CTCCCGTAAACGATGGTCTGGTCTCGTGTTCAGGAGACTGTCGTGTAAGAACCATGAGTA
       uArgAlaPheAlaThrArgProGluHisLysSerSerAspSerThrPheLeuValLeuMe

GTCTCATGGCATCCTGGAGGGAATCTGCGGAACTGTGCATGATGAGAAAAAACCAGATGT
661    ------+------+------+------+------+------+  720
       CAGAGTACCGTAGGACCTCCCTTAGACGCCTTGACACGTACTACTCTTTTTTGGTCTACA
       tSerHisGlyIleLeuGluGlyIleCysGlyThrValHisAspGluLysLysProAspVa

GCTGCTTTATGACACCATCTTCCAGATATTCAACAACCGCAACTGCCTCAGTCTGAAGGA
721    ------+------+------+------+------+------+  780
       CGACGAAATACTGTGGTAGAAGGTCTATAAGTTGTTGGCGTTGACGGAGTCAGACTTCCT
       lLeuLeuTyrAspThrIlePheGlnIlePheAsnAsnArgAsnCysLeuSerLeuLysAs

CAAACCCAAGGTCATCATTGTCCAGGCCTGCAGAGGTGCAAACCGTGGGGAACTGTGGGT
781    ------+------+------+------+------+------+  840
       GTTTGGGTTCCAGTAGTAACAGGTCCGGACGTCTCCACGTTTGGCACCCCTTGACACCCA
       pLysProLysValIleIleValGlnAlaCysArgGlyAlaAsnArgGlyGluLeuTrpVa

CAGAGACTCTCCAGCATCCTTGGAAGTGGCCTCTTCACAGTCATCTGAGAACCTGGAGGA
841    ------+------+------+------+------+------+  900
       GTCTCTGAGAGGTCGTAGGAACCTTCACCGGAGAAGTGTCAGTAGACTCTTGGACCTCCT
       lArgAspSerProAlaSerLeuGluValAlaSerSerGlnSerSerGluAsnLeuGlul AGATGCTGTTTACAAGACCCACGTGGAGAAGGACTTCATTGCTTTCTGCTCTTCAACGCC
901    ------+------+------+------+------+------+  960
       TCTACGACAAATGTTCTGGGTGCACCTCTTCCTGAAGTAACGAAAGACGAGAAGTTGCGG
       uAspAlaValTyrLysThrHisValGluLysAspPheIleAlaPheCysSerSerThrPr
```

FIG. 1B

```
        ACACAACGTGTCCTGGAGAGACAGCACAATGGGCTCTATCTTCATCACACAACTCATCAC
961     ————+————+————+————+————+————+ 1020
        TGTGTTGCACAGGACCTCTCTGTCGTGTTACCCGAGATAGAAGTAGTGTGTTGAGTAGTG
        oHisAsnValSerTrpArgAspSerThrMetGlySerIlePheIleThrGlnLeuIleTh

ATGCTTCCAGAAATATTCTTGGTGCTGCCACCTAGAGGAAGTATTTCGGAAGGTACAGCA
1021    ————+————+————+————+————+————+ 1080
        TACGAAGGTCTTTATAAGAACCACGACGGTGGATCTCCTTCATAAAGCCTTCCATGTCGT
        rCysPheGlnLysTyrSerTrpCysCysHisLeuGluGluValPheArgLysValGlnGl

ATCATTTGAAACTCCAAGGGCCAAAGCTCAAATGCCCACCATAGAACGACTGTCCATGAC
1081    ————+————+————+————+————+————+ 1140
        TAGTAAACTTTGAGGTTCCCGGTTTCGAGTTTACGGGTGGTATCTTGCTGACAGGTACTG
        nSerPheGluThrProArgAlaLysAlaGlnMetProThrIleGluArgLeuSerMetTh

AAGATATTTCTACCTCTTTCCTGGCAATTGAAAATGGAAGCCACAAGCAGCCCAGCCCTC
1141    ————+————+————+————+————+————+ 1200
        TTCTATAAAGATGGAGAAAGGACCGTTAACTTTTACCTTCGGTGTTCGTCGGGTCGGGAG
        rArgTyrPheTyrLeuPheProGlyAsnEnd

CTTAATCAACTTCAAGGAGCACCTTCATTAGTACAGCTTGCATATTTAACATTTTGTATT
1201    ————+————+————+————+————+————+ 1260
        GAATTAGTTGAAGTTCCTCGTGGAAGTAATCATGTCGAACGTATAAATTGTAAAACATAA

TCAATAAAAGTGAAGACAAACAAAAAAAAAAAAAAAA
1261    ————+————+————+———— 1297
        AGTTATTTTCACTTCTGTTTGTTTTTTTTTTTTTTTT
```

FIG.1C

```
  1  MAEGNHRKKPLKVLESLGKDFLTGVLDNLVEQNVLNWKEEEKKKYYDAKT   50
     ||:  :.|.  .: |:|.: :.|:||:|:: .|||..| ||| | :|..
  1  MADKVLKEKRKLFIRSMGEGTINGLLDELLQTRVLNKEEMEKVKRENATV   50

51  EDKVRVMADSMQEKQRMAGQM..........LLQTF.FNIDQISPNK..   86
     ||.|.: ||: .|. |.|:         | .|: :. ||.|.|
 51  MDKTRALIDSVIPKGAQACQICITYICEEDSYLAGTLGLSADQTSGNYLN  100

87  ..........KAHPNMEAGP..PESGESTDALKLCPHEEFLRLCKERAE  123
               .|......:..|  |.|.::|.::|||. || |: |:..
101  MQDSQGVLSSFPAPQAVQDNPAMPTSSGSEGNVKLCSLEEAQRIWKQKSA  150

124  EIYPIKERNNRTRLALIICNTEFDHLPPRNGADFDITGMKELLEGLDYSV  173
     |||||.::..||||||||||.||| :|.|.||:.||||. ||:.|:|||
151  EIYPIMDKSSRTRLALIICNEEFDSIPRRTGAEVDITGMTMLLQNLGYSV  200

174  DVEENLTARDMESALRAFATRPEHKSSDSTFLVLMSHGILEGICGTVHDE  223
     ||..||||.||...| |||  |||||.||||||:||||| |||||. |.|
201  DVKKNLTASDMTTELEAFAHRPEHKTSDSTFLVFMSHGIREGICGKKHSE  250

224  KKPDVLLYDTIFQIFNNRNCLSLKDKPKVIIVQACRGANRGELWVRDSPA  273
     . ||:| .:.||.::|.:|| |||||||||||||:|||| | :|.:||.:
251  QVPDILQLNAIFNMLNTKNCPSLKDKPKVIIIQACRGDSPGVVWFKDSVG  300

274  SLEVASSQSSENLEEDAVYKTHVEKDFIAFCSSTPHNVSWRDSTMGSIFI  323
     :  | ...|::|:||: |.|:||||||||||||.||||..||||:||
301  VSGNLSLPTTEEFEDDAIKKAHIEKDFIAFCSSTPDNVSWRHPTMGSVFI  350

324  TQLITCFQKYSWCCHLEEVFRKVQQSFETPRAKAQMPTIERLSMTRYFYL  373
     ..||. :|.|. :|.:||||. ||| | :::|||||.||:.:||:|||
351  GRLIEHMQEYACSCDVEEIFRKVRFSFEQPDGRAQMPTTERVTLTRCFYL  400

374  FPGN.  377
     |||:
401  FPGH*  405
```

FIG.2

```
  1 MAEGNHRKKPLKVLESLGKDF.LTGVLDNLVEQNVLNWKEEEKKKYYDAK  49
    | .::|.   : :   :...: :..::|: |:...|||.::::. . :::
  1 MMRQDRRSLLERNIMMFSSHLKVDEILEVLIAKQVLNSDNGDMINSCGT.  49

50 TEDKVRVMADSMQEKQRMAGQMLLQTFFNIDQ..................  81
    . :| |  :...:| :. :|  :   :.:..  ...::
 50 VREKRREIVKAVQRRGDVAFDAFYDALRSTGHEGLAEVLEPLARSVDSNA  99

82 ..................ISPNKKAHPNMEAGPPESGESTDALKLCP.... 110
                     || .| |.  ..::  .|  :....|  .:.
150 RSRSRSRALHSSDRHNYSSPPVNAFPSQPSSANSSFTGCSSLGYSSSRNR 199

111 ..............HEEFLRLCKERA.....EEIYPIKERNNRTRLALIIC 142
                |||  ::......     :|   .::  ...  :.|||
200 SFSKASGPTQYIFHEEDMNFVDAPTISRVFDEKTMYRNFSSPRGMCLIIN 249

250 NEHFEQMPTRNGTKADKDNLTNLFRCMGYTVICKDNLTGRGMLLTIRDFA 299

193 TRPEHKSSDSTFLVLMSHGILEGICGTVHDEKKPDVLLYDTIFQIFNNRN 242
    .:..|   :||.:||::|||  :.|.| |.| ...    ..|::::|. |
300 KHESH..GDSAILVILSHGEENVIIG.VDDIPIST....HEIYDLLNAAN 342

243 CLSLKDKPKVIIVQACRGANRGELW.....VRDSPASLEVASSQSSENL. 286
    ..| :|||:::|||||..|:: :     |:|| |  :......: |
343 APRLANKPKIVFVQACRGERRDNGFPVLDSVDGVPAFLRRGWDNRDGPLF 392

287 ........EEDAVY.KTHVEKDFIAFCSSTPHNVSWRDSTMGSIFITQLI 327
            : :.|: |... : |::  :..|::  ||||:|..|| || .:.
393 NFLGCVRPQVQQVWRKKPSQADILIRYATTAQYVSWRNSARGSWFIQAVC 442

328 TCFQKYSW....CCHLEEVFRKVQQSFETPRAKAQMPTIERLS..MTRYF 371
    ..| ....    . |.|| :||. .:|:|......  :. :. ..: :  |
443 EVFSTHAKDMDVVELLTEVNKKVACGFQTSQGSNILKQMPEMTSRLLKKF 492

372 YLFPGN...... 377
    |::|:.
493 YFWPEARNSAV* 504
```

FIG.3

```
151  PRNGADFDITGMKELLEGLDYSVDVEENLTARDMESALRAFATRPEHKSS  200
                                       | . . |..:|:|
  1  ................................MLTVQVYRTSQKCS   14

201  DSTFLVLMSHGILEGICGTVHDEKKPDVLLYDTIFQIFNNRNCLSLKDKP  250
     .|. :|   ..:|:.:..... .  .|.:|||:|
 15  SSKHVV...EVLLDPLGTSFCSLLPPLLLYETD.................  45

251  KVIIVQACRGANRGELWVRDSPASLEVASSQSSENLEEDAVYKTHVEKDF  300
     ||.:..:       :.  . ..::.:|... ||    : .. .|:
 46  ........RGVDQQD....GKNHTQSPGCEESDAGKEELMKMRLPTRSDM  83

301  IAFCSSTPHNVSWRDSTMGSIFITQLITCFQKYSWCCHLEEVFRKVQQSF  350
     |. :.: . |.. |:...|| :|..|. .| . .    |:.::: ||.. :
 84  ICGYACLKGNAAMRNTKRGSWYIEALTQVFSERACDMHVADMLVKVNALI  133

351  ETPRAKAQMPTIER........LSMTRYFYLFPGN....  377
     ... : |. ...:|           .:.. :|||||
134  KEREGYAPGTEFHRCKEMSEYCSTLCQQLYLFPGYPPT*  172
```

FIG.4

INTERLEUKIN-1β CONVERTING ENZYME-RELATED CYSTEINE PROTEINASE II (ICE$_{REL}$-II)

CROSS-RELATED TO OTHER APPLICATIONS

This is a continuation of U.S. Ser. No. 08/225,487, filed Apr. 8, 1994, now pending and is the U.S. national phase of International Patent Application No. PCT/CA95/00188, filed Apr. 4, 1995.

BACKGROUND OF THE INVENTION

Interleukin-1β (IL-1β) is a major mediator of chronic and acute inflammation. Along with IL-1β, human monocytes produce two additional members of the IL-1 gene family; interleukin-1α (IL-1α) and IL-1 receptor antagonist (IL-RA). All three proteins bind to the membrane-anchored forms of the type 1 and type 2 IL-1 receptors (IL1R) on target cells. IL-1α and IL-1β elicit virtually identical biological responses whereas IL-1RA blocks these effects. Both IL-1α and IL1β are synthesized as 31 kDa primary translation products which lack functional hydrophobic signal sequences. The 31 kDa form of IL-1α is fully active without further processing but does not appear to be actively released from cells. IL-1β, the predominant form of IL-1 released by activated monocytes, is synthesized as an inactive 31 kDa precursor (pIL-1β) that is processed to its mature 17.5 kDa form (mIL-1β) by interleukin-1β converting enzyme (ICE), a novel cysteine proteinase. ICE generates fully active mIL-1β by cleaving pIL-1β between Asp$_{116}$ and Ala$_{117}$, a unique site for prohormone processing. The sequence around this cleavage site, -Tyr-Val-His-Asp-Ala-, is evolutionarily conserved in all known pIL-1β polypeptides.

Active human ICE as shown by conventional HPLC and affinity purification techniques is a heterodimer consisting of a 1:1 stoichiometric complex of 19,866 Da (p20) and 10,244 Da (p10) subunits. Cloned cDNAs have revealed that ICE is constituitively expressed as a 45 kDa proenzyme (p45) composed of a 14 kDa prodomain, followed by p20 which contains the active site Cys$_{285}$, a 19 residue connecting peptide that is not present in the mature enzyme, and p10, a required component of the active enzyme. The mature subunits are flanked by Asp-X sequences. Mutational analysis of these sites and expression in heterologous systems indicates that the generation of active enzyme is autocatalytic. Murine and rat ICE have also been cloned and show a high degree of sequence similarity including these structural motifs.

Recently, a family of ICE-like genes has begun to emerge, including the nematode cell death abnormal gene (CED-3) of *Caenorhabiditis elegans, Caenorhabiditis briggsae* and *Caenorhabiditis vulgaris*, and the murine neuronal precursor cell embroyonic developmentally downregulated (NEDD-2) gene. The predicted polypeptide sequences of these genes exhibit 29% and 27% sequence identity with human ICE, respectively. The sequence identity of CED-3 with ICE is higher in the regions corresponding to the p20 and p10 subunits of mature human ICE. All known sequences for ICE and for CED-3 contain the pentapeptide sequence -Gln-Ala-Cys-Arg-Gly- surrounding the catalytic cysteine of ICE or its equivalent in CED-3.

Both CED-3 and murine ICE, when expressed by transfection in fibroblast cell lines or by microinjection into neuronal cells, cause programmed cell death (apoptosis) to occur. The pro-apoptotic effects of CED-3 or ICE can be prevented by co-transfection with either bcl-2, a mammalian proto-oncogene which appears to function as a cell death suppressor gene, or with the cytokine response modifier A (crmA) gene product, a serpin-like inhibitor of ICE.

SUMMARY OF THE INVENTION

A novel human thiol proteinase termed ICE$_{rel}$-II (interleukin-1β converting enzyme—related cysteine proteinase II) has been isolated and purified. A DNA molecule encoding the full length precursor form of the ICE$_{rel}$-II protein has been isolated, purified and the nucleotide sequence determined. The ICE$_{rel}$-II encoding DNA has been cloned for expression in recombinant hosts. The DNA clones produce recombinant full-length ICE$_{rel}$-II and the individual subunits of the mature form of the enzyme. Recombinant ICE$_{rel}$-II is useful for identifying modulators of ICE$_{rel}$-II activity and hence modifiers of pathological conditions related to the pro-inflammatory or pro-apoptotic effects of ICE$_{rel}$-II. ICE$_{rel}$-II antisense molecules are useful for therapeutically reducing or eliminating the pro-inflammatory or pro-apoptotic effects of ICE$_{rel}$-II, whereas gene transplantation or gene therapy with ICE$_{rel}$-II is useful for enhancing the pro-inflammatory or pro-apoptotic effects of ICE$_{rel}$-II. These therapies are beneficial in the treatment of immune, proliferative and degenerative diseases including, but not limited to, immune deficiency syndromes (such as AIDS), autoimmnune diseases, pathogenic infections, cardiovascular and neurological injury, alopecia, aging, cancer, Parkinson's disease and Alzheimer's disease.

BRIEF DESCRIPTION OF THE DRAWINGS

FIGS. 1A–1C. Nucleotide sequence of human ICE$_{rel}$-II (cDNA clone P101.1.1), its complementary nucleotide sequence, and deduced amino acid sequence.

FIG. 2. Alignment of the human ICE$_{rel}$-II amino acid sequence with the amino acid sequence of human ICE. Identical amino acids are indicated by a vertical line between the aligned sequences, whereas highly conservative amino acid differences are indicated by a double dot and conservative amino acid differences are indicated by a single dot between the aligned sequences.

FIG. 3. Alignment of the human ICE$_{rel}$-II amino acid sequence with the amino acid sequence of *Caenorhabiditis elegans* CED-3. Identical amino acids are indicated by a vertical line between the aligned sequences, whereas highly conservative amino acid differences are indicated by a double dot and conservative amino acid differences are indicated by a single dot between the aligned sequences.

FIG. 4. Alignment of the human ICE$_{rel}$-II amino acid sequence with the amino acid sequence of murine NEDD-2. Identical amino acids are indicated by a vertical line between the aligned sequences, whereas highly conservative amino acid differences are indicated by a double dot and conservative amino acid differences are indicated by a single dot between the aligned sequences.

DETAILED DESCRIPTION OF THE INVENTION

A complementary DNA (cDNA) which encodes the full length form of ICE$_{rel}$-II is identified, sequenced and isolated. The cDNA is cloned into expression vectors for expression in a recombinant host. The cDNA is useful to produce recombinant full length ICE$_{rel}$-II. The cDNA and the recombinant ICE$_{rel}$-II protein derived therefrom are useful in the production of antibodies, diagnostic kits, laboratory reagents and assays. The cDNA and the recombinant ICE$_{rel}$-II protein may be used to identify compounds that affect $ICE_{rel}$-II function, inflammation and cell apoptosis. $ICE_{rel}$-II antisense oligonucleotides or antisense mimetics may be clinically useful for reducing the expression of $ICE_{rel}$-II protein and thereby reducing the pro-inflammatory or pro-apoptotic effects of $ICE_{rel}$-II. Similarly, the $ICE_{rel}$-II coding sequence can be used for gene therapy to introduce $ICE_{rel}$-II into target cells thereby enhancing the pro-inflammatory or pro-apoptotic effects of $ICE_{rel}$-II.

A variety of cells and cell lines may be suitable for use to isolate $ICE_{rel}$-II cDNA. Selection of suitable cells may be done by screening for $ICE_{rel}$-II activity in cell extracts or conditioned medium using conventional techniques. Cells which possess $ICE_{rel}$-II activity in this assay may be suitable for the isolation of $ICE_{rel}$-II cDNA.

A variety of procedures may be used to molecularly clone $ICE_{rel}$-II cDNA. These methods include, but are not limited to, direct functional expression of the $ICE_{rel}$-II gene following the construction of an $ICE_{rel}$-II-containing cDNA library in an appropriate expression vector system. Another method is to screen an $ICE_{rel}$-II-containing cDNA library constructed in a bacteriophage or plasmid shuttle vector with a labelled oligonucleotide probe designed from the amino acid sequence of $ICE_{rel}$-II.

A variety of libraries constructed from cells may be useful for isolating $ICE_{rel}$-II-encoding DNA. Suitable libraries may be prepared from cells or cell lines which have $ICE_{rel}$-II activity.

Preparation of cDNA libraries can be performed by standard techniques known in the art. Such cDNA library construction techniques as well as other standard molecular biology techniques can be found, for example, in Maniatis, T., Fritsch, E. F., Sambrook, J., *Molecular Cloning: A Laboratory Manual* (Cold Spring Harbor Laboratory, Cold Spring Harbor, New York, 1982) or in Ausubel, F. M., Brent, R., Kingston, R. E., Moore, D. D., Seidman, J. G., Smith, J. A., Struhl, K., *Current Protocols in Molecular Biology* (John Wiley & Sons, New York, New York, 1989).

DNA encoding $ICE_{rel}$-II may also be isolated from a suitable genomic DNA library. Construction of genomic DNA libraries can be performed by standard techniques known in the art. Known genomic DNA library construction techiques can be found in Maniatis, T. et al., (supra), Ausubel et al., (supra).

The cloned $ICE_{rel}$-II cDNA may be recombinantly expressed by molecular cloning into an expression vector containing a suitable promoter and other appropriate transcription regulatory elements, and transferred into prokaryotic or eukaryotic host cells to produce recombinant $ICE_{rel}$-II.

Expression vectors are defined herein as DNA sequences that are required for the transcription of cloned copies of genes and the translation of their mRNAs in an appropriate host. Such vectors can be used to express eukaryotic genes in a variety of hosts such as bacteria, yeast, bluegreen algae, plant cells, insect cells and animal cells.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant $ICE_{rel}$-II in mammalian cells. Commercially-available mammalian expression vectors which may be suitable for recombinant $ICE_{rel}$-II expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

DNA encoding $ICE_{rel}$-II may also be cloned into an expression vector for expression in a recombinant host cell. Recombinant host cells may be prokaryotic or eukaryotic, including but not limited to bacteria, yeast, mammalian cells and insect cells. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, infection, protoplast fusion, and electroporation. The expression vector-containing cells are clonally propagated and individually analyzed to determine whether they produce $ICE_{rel}$-II protein. Identification of $ICE_{rel}$-II expressing host cell clones may be done by several means, including but not limited to immunological reactivity with anti-$ICE_{rel}$-II antibodies, and the presence of host cell-associated $ICE_{rel}$-II activity.

Expression of $ICE_{rel}$-II cDNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the $ICE_{rel}$-II cDNA sequence(s) that yields optimal levels of enzymatic activity and/or $ICE_{rel}$-II protein, modified $ICE_{rel}$-II cDNA molecules are constructed. Host cells are transformed with the cDNA molecules and the levels of $ICE_{rel}$-II RNA and protein are measured.

Levels of $ICE_{rel}$-II protein in host cells are quantitated by a variety of methods such as immunoaffmity and/or ligand affinity techniques. $ICE_{rel}$-II-specific affinity beads or $ICE_{rel}$-II-specific antibodies are used to isolate $^{35}$S-methionine labelled or unlabelled $ICE_{rel}$-II protein. Labelled $ICE_{rel}$-II protein is analyzed by SDS-PAGE. Unlabelled $ICE_{rel}$-II protein is detected by Western blotting, ELISA or RIA assays employing $ICE_{rel}$-II specific antibodies.

Following expression of $ICE_{rel}$-II in a recombinant host cell, $ICE_{rel}$-II protein may be recovered to provide $ICE_{rel}$-II in active form. Several $ICE_{rel}$-II purification procedures are available and suitable for use. Recombinant $ICE_{rel}$-II may be purified from cell lysates or from conditioned culture media, by various combinations of, or individual application of fractionation, or chromatography steps that are known in the art.

In addition, recombinant $ICE_{rel}$-II can be separated from other cellular proteins by use of an immuno-affinity column made with monoclonal or polyclonal antibodies specific for full length nascent $ICE_{rel}$-II or polypeptide fragments of $ICE_{rel}$-II.

The recombinant protein may be used to generate antibodies. The term "antibody" as used herein includes both polyclonal and monoclonal antibodies, as well as fragments thereof, such as, Fv, Fab and F(ab)2 fragments that are capable of binding antigen or hapten.

Monospecific antibodies to $ICE_{rel}$-II are purified from mammalian antisera containing antibodies reactive against $ICE_{rel}$-II or are prepared as monoclonal antibodies reactive with $ICE_{rel}$-II using standard techniques. Monospecific antibody as used herein is defined as a single antibody species or multiple antibody species with homogenous binding characteristics for $ICE_{rel}$-II. Homogenous binding as used herein refers to the ability of the antibody species to bind to a specific antigen or epitope, such as those associated with the $ICE_{rel}$-II, as described above. Enzyme-specific antibodies are raised by immunizing animals such as mice, rats, guinea pigs, rabbits, goats, horses and the like, with rabbits being preferred, with an appropriate concentration of $ICE_{rel}$-II either with or without an immune adjuvant.

Monoclonal antibodies (mAb) reactive with $ICE_{rel}$-II may be prepared by conventional methods, such as by immunizing inbred mice with $ICE_{rel}$-II. The mice are immunized with about 0.1 mg to about 10 mg, preferably about 1 mg, of $ICE_{rel}$-II in about 0.5 ml buffer or saline incorporated in an equal volume of an acceptable adjuvant. Freund's complete adjuvant is preferred. The mice receive an initial immunization on day 0 and are rested for about 3 to about 30 weeks. Immunized mice are given one or more booster immunizations of about 0.1 to about 10 mg of $ICE_{rel}$-II in a buffer solution such as phosphate buffered saline (PBS) by the intravenous (IV) route. Lymphocytes from antibody-positive mice are obtained by removing spleens from immunized mice by standard procedures known in the art. Hybridoma cells are produced by mixing the splenic lymphocytes with an appropriate fusion partner under conditions which will allow the formation of stable hybridomas. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody produciton by an immunoassay such as solid phase immunoradioassay (SPIRA) using $ICE_{rel}$-II as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

In vitro production of anti-$ICE_{rel}$-II is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of $ICE_{rel}$-II in body fluids or tissue and cell extracts.

Methods such as those described above may be used to produce monospecific antibodies may be utilized to produce antibodies specific for $ICE_{rel}$-II polypeptide fragments or full-length nascent $ICE_{rel}$-II polypeptide.

$ICE_{rel}$-II antibody affinity columns are made by adding the antibodies to a gel support, such as Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing $ICE_{rel}$-II or $ICE_{rel}$-II fragments are slowly passed through the column. The column is then washed, and the protein is eluted. The purified $ICE_{rel}$-II protein is then dialyzed against phosphate buffered saline.

Kits containing $ICE_{rel}$-II cDNA, antibodies to $ICE_{rel}$-II or $ICE_{rel}$-II protein may be prepared. Such kits are used to detect DNA which hybridizes to $ICE_{rel}$-II DNA or to detect the presence of $ICE_{rel}$-II protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of $ICE_{rel}$-II DNA, $ICE_{rel}$-II RNA or $ICE_{rel}$-II protein. The recombinant proteins, DNA molecules, RNA molecules and antibodies lend themselves to the formulation of kits suitable for the detection and typing of $ICE_{rel}$-II. Such a kit would comprise a compartmentalized carrier suitable to hold in close confinement at least one container. The carrier would further comprise reagents such as recombinant $ICE_{rel}$-II protein or anti-$ICE_{rel}$-II antibodies suitable for detecting $ICE_{rel}$-II. The carrier may also contain means for detection such as labeled antigen or enzyme substrates or the like.

Nucleotide sequences that are complementary to the $ICE_{rel}$-II encoding cDNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other $ICE_{rel}$-II antisense oligonucleotide mimetics. $ICE_{rel}$-II antisense molecules may be introduced into cells by microinjection, liposome encapsulation or by expression from vectors harbouring the antisense sequence. $ICE_{rel}$-II antisense therapy may be particularly useful for the treatment of diseases where it is beneficial to reduce $ICE_{rel}$-II acitivy.

$ICE_{rel}$-II gene therapy may be used to introduce $ICE_{rel}$-II into the cells of target organs. The $ICE_{rel}$-II gene can be ligated into viral vectors which mediate transfer of the $ICE_{rel}$-II DNA by infection of recipient host cells. Suitable viral vectors include retrovirus, adenovirus, adeno-associated virus, herpes virus, vaccinia virus, polio virus and the like. Alternatively, $ICE_{rel}$-II DNA can be transferred into cells for gene therapy by non-viral techniques including receptor-mediated targetted DNA transfer using ligand-DNA conjugates or adenovirus-ligand-DNA conjugates, lipofection membrane fusion or direct microinjection. These procedures and variations of them are suitable for ex vivo as well as in vivo $ICE_{rel}$-II gene therapy. $ICE_{rel}$-II gene therapy may be particularly useful for the treatment of diseases where it is beneficial to elevate $ICE_{rel}$-II activity.

Pharmaceutically useful compositions comprising $ICE_{rel}$-II DNA or $ICE_{rel}$-II protein may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein or DNA.

Therapeutic or diagnostic compositions of the invention are administered to an individual in amounts sufficient to treat or diagnose $ICE_{rel}$-II related disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

Because the genetic code is degenerate, more than one codon may be used to encode a particular amino acid, and therefore, the amino acid sequence can be encoded by any of a set of similar DNA oligonucleotides. Only one member of the set will be identical to the $ICE_{rel}$-II sequence but will be capable of hybridizing to $ICE_{rel}$-II DNA even in the presence of DNA oligonucleotides with mismatches. The mismatched DNA oligonucleotides may still hybridize to the $ICE_{rel}$-IIDNA to permit identification and isolation of $ICE_{rel}$-II encoding DNA.

DNA encoding $ICE_{rel}$-II from a particular organism may be used to isolate and purify homologues of $ICE_{rel}$-II from other organisms. To accomplish this, the first $ICE_{rel}$-II DNA may be mixed with a sample containing DNA encoding homologues of $ICE_{rel}$-II under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate.

As used herein, a "functional derivative" of $ICE_{rel}$-II is a compound that possesses a biological activity (either functional or structural) that is substantially similar to the biological activity of $ICE_{rel}$II. The term "functional derivatives" is intended to include the "fragments," "variants," "degenerate variants," "analogs" and "homologs" or to "chemical derivatives" of $ICE_{rel}$-II. The term "fragment" is meant to refer to any polypeptide subset of $ICE_{rel}$-II. The term "variant" is meant to refer to a molecule substantially similar in structure and function to either the entire $ICE_{rel}$-II molecule or to a fragment thereof. A molecule is "substantially similar" to $ICE_{rel}$-II if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire $ICE_{rel}$-II molecule or to a fragment thereof.

The term "chemical derivative" describes a molecule that contains additional chemical moieties which are not normally a part of the base molecule. Such moieties may improve the solublity, half-life, absorption, etc of the base molecule. Alternatively the moieties may attenuate undesirable side effects of the base molecule or decrease the toxicity of the base molecule. Examples of such moieties are described in a variety of texts, such as Remington's Pharmaceutical Sciences.

The present invention is also directed to methods for screening for compounds which modulate that expression of DNA or RNA encoding $ICE_{rel}$-II as well as the function of $ICE_{rel}$-II protein in vivo. Compounds which modulate these activities may be DNA, RNA, peptides, proteins, or non-proteinaceous organic molecules. Compounds may modulate by increasing or attenuating the expression of DNA or RNA encoding $ICE_{rel}$-II or the function of $ICE_{rel}$-II protein. Compounds that modulate the expression of DNA or RNA encoding $ICE_{rel}$-II or the function of $ICE_{rel}$-II protein may be detected by a variety of assays. The assay may be a simple "yes/no" assay to determine whether there is a change in expression or function. The assay may be made quantitative by comparing the expression or function of a test sample with the levels of expression or function in a standard sample.

The following examples illustrate the present invention without, however, limiting the same thereto.

EXAMPLE 1

Molecular Cloning of $ICE_{rel}$-II

A partial-length cDNA clone for $ICE_{rel}$-II was identified by replica-filter screening of a THP-1 cell (acute monocytic leukemia cell line; ATCC TIB 202) cDNA library in bacteriophage λgt10 using the [$^{32}$P]-labelled synthetic oligonucleotide probe:

(5')-ATG AAG GAT GAG GTG GCC CTG CTG GCT GCT GTG ACC CTG CTG GGC GTG CTG CTG CAG GCT GGC TTC TCC CTG CAG GTG ATC TCT GCC CGG ATT GCC TTC CGG GT(3') (SEQ ID NO:1).

This initial 748 bp clone, designated T10.3.1, corresponded to bases 544–1291 of the full-length $ICE_{rel}$-II clone described herein. The clone was retrieved from an individual λgt10 plaque by DNA amplification using the polymerase chain reaction (PCR) with the synthetic oligonucleotide primers (5')TGA GCA AGT TCA GCC TGG TTA AGT(3') (SEQ ID NO 2; forward primer) and (5'GGC TTA TGA GTA TTT CTT CCA GGG(3') (SEQ ID NO:3; reverse primer)

which correspond to the sequence of λgt10 on the left and right side, respectively, of the Eco RI restriction enzyme site containing the cDNA insert. The resulting amplification product was ligated into the plasmid vector pCR-II (Invitrogen), transformed into competent *Escherichia coli* cells, colony-purified and propagated by growth of the resulting transformed cells in liquid culture. The plasmid DNA was purified from the cells and the nucleotide sequence of the clone T10.3.1 insert was determined by dideoxy DNA sequencing. Based on the sequence of this clone, synthetic oligonucleotides specific for the clone T10.3.1 sequence were prepared and after [$^{32}$p] labelling were used to re-screen the THP-1 cell λgt10 cDNA library. The probes used for replica filter screening were (5')AGG CCA CTT CCA AGG ATG CTG GA(3') SEQ ID NO:4 (one replica filter) and (5')CTG GAA GAT GGT GTC ATA AAG CAG C(3') SEQ ID NO:5 (other paired replica filter).

The largest clone identified, designated T15.1.1, was 1207 bp and corresponded to bases 64–1270 of the full-length ICE$_{rel}$-II clone described herein. The clone was retrieved from λgt10 following expansion of the λ bacteriophage by culture on E. coli-containing agarose plates, then purifying the λ bacteriophage DNA by a combination of polyethylene glycol precipitation, macroporous silica-gel chromatography and alcohol precipitation. The T15.1.1 DNA fragment was excised by partial Eco RI restriction digestion (partial digestion was necessary owing to an internal Eco RI site in the T15.1.1 sequence) followed by agarose gel purification of the 1.2 Kb fragment then ligation of the purified fragment into the Eco RI site of the plasmid vector pBluescript II SK+ (Stratagene). Following transformation into competent E. coli cells, colony purification and propagation of the resulting transformed cells in liquid culture, the plasmid DNA was purified and the nucleotide sequence of the clone T15.1.1 fragment was determined.

The full-length ICE$_{rel}$-II clone (designated P101.1.1) was identified by replica filter screening of a human peripheral blood monocyte cDNA library in bacteriophage λgt11. The filters were probed with a [$^{32}$P]-labelled PCR fragment that had been generated by amplification of the T15.1.1 ICE$_{rel}$-II clone using the primers (5')GAA CTG GAA GGA AGA GGA AA(3') (SEQ ID NO: 6; forward primer) and (5')TCA TGC ACA GTT CCG CAG ATT CCC T(3') (SEQ ID NO:7; reverse primer)

which produced a fragment corresponding to bases 142–702 of the full-length ICE$_{rel}$-II sequence. (This probe was chosen since it was in a region of ICE$_{rel}$-II with low sequence identity to ICE and would therefore minimize the number of ICE clones identified.) The 1297 bp full-length ICE$_{rel}$-II clone (P101.1.1) was retrieved by Eco RI excision from purified λ bacteriophage DNA as described above for clone T15.1.1. The DNA sequence of the P101.1.1 ICE$_{rel}$-II clone was identical to four other clones that were isolated during the same series of replica filter screens.

The complete cDNA sequence of ICE$_{rel}$-II (clone P101.1.1) and corresponding amino acid sequence is shown in FIG. 1. The longest open reading frame of ICE$_{rel}$-II clone P101.1.1 (bases 38 to 1168) encodes a 43.3 kDa polypeptide which has 53% sequence identity (68% sequence similarity) with human interleukin-1β converting enzyme (FIG. 2), 26% sequence identity (52% sequence similarity) with the Caenorhabiditis elegans CED-3 polypeptide (FIG. 3) and 23% sequence identity (41% sequence similarity) with the murine NEDD-2 polypeptide (FIG. 4). The particularly high degree of sequence conservation surrounding the catalytic cysteine residue (Cys$_{258}$ of ICE$_{rel}$-II, Cys$_{285}$ of human interleukin-1β converting enzyme, Cys$_{358}$ of CED-3) as well as other structural motifs throughout the polypeptide is consistent with ICE$_{rel}$-II being a thiol proteinase.

EXAMPLE 2

Sub-Cloning of the ICE$_{rel}$-II cDNA Into Expression Vectors

The cDNA encoding ICE$_{rel}$-II was sub-cloned into several vectors for expression of the ICE$_{rel}$-II protein in transfected host cells and for in vitro transcription/translation. These vectors include pBluescript II SK+ (where expression is driven by T7 or T3 promoters), pcDNA I/Amp (where expression is driven by the cytomegalovirus (CMV) promoter), pSZ9016-1 (where expression is driven by the HIV long terminal repeat (LTR) promoter) and the baculovirus transfer vector pVL1393 (where expression is driven by the polyhedrin (PH) promoter) for producing recombinant baculovirus containing the ICE$_{rel}$-II encoding DNA sequence. Using techniques such as those described in Maniatis (supra) and Ausubel (supra), ICE$_{rel}$-II may be subcloned into vectors suitable for expression in bacteria or yeast or other expression systems. The predicted/actual amino acid sequence of ICE$_{rel}$-II is shown in FIG. 1.

a) pBluescript II SK+:ICE$_{rel}$-II. The full length ICE$_{rel}$-II cDNA clone was retrieved from λ bacteriophage by limited Eco RI digestion and ligated into Eco RI-cut, CIP-treated pBluescript II SK+ as described above under "molecular cloning of ICE$_{rel}$-II". Separate subclones were recovered in which the sense orientation of ICE$_{rel}$-II followed either the T7 or T3 promoters.

b) pcDNA I/Amp:ICE$_{rel}$-II. In order to enable directional cloning, ICE$_{rel}$-II was excised from a purified plasmid preparation of pBluescript II SK+:ICE$_{rel}$-II ('a'above) in which the ICE$_{rel}$-II DNA sequence was downstream of the T7 promoter using Eco RV and Xba I. The resulting Eco RV, Xba I ICE$_{rel}$-II fragment was purified and ligated into Eco RV-cut, Xba I-cut, CIP-treated pcDNA I/Amp such that the ICE$_{rel}$-II encoding DNA was downstream of the CMV promoter.

c) pSZ9016-1:ICE$_{rel}$-II. ICE$_{rel}$-II was excised from pBluescript II SK+:ICE$_{rel}$-II ('a'above) by limited Eco RI digestion and subsequent purification of the 1.3 Kb fragment from agarose gels. The resulting Eco RI ICE$_{rel}$-II fragment was ligated into Eco RI-cut, CIP-treated pSZ9016-1. Subclones were selected in which the sense orientation of ICE$_{rel}$-II was downstream of the HIV LTR promoter.

d) pVL1393:ICE$_{rel}$-II and pVL1393:T7 ICE$_{rel}$-II HA

Directional cloning of the ICE$_{rel}$-II encoding DNA into the baculovirus transfer vector pVL1393 was mediated by excising ICE$_{rel}$-II from pcDNA I/Amp:ICE$_{rel}$-II ('b' above) with Bam HI and Xba I then ligating the resulting 1.3 Kb fragment into Bam HI-cut, Xba I-cut, CIP-treated pVL1393 producing pVL1393:ICE$_{rel}$-II. Similarly, ICE$_{rel}$-II was epitope tagged by engineering a T7 tag at the 5' amino terminus of the ICE$_{rel}$-II open reading frame and a FluHA epitope at the 3' carboxy terminus. The ICE$_{rel}$-II DNA modified in this manner was ligated into the Bam HI/Xba I sites of pVL1393 to produce pVL1393:T7 ICE$_{rel}$-II HA.

EXAMPLE 3

Expression of the ICE$_{rel}$-II Polypeptide by In Vitro Transcription/Translation and by Transfection Into Host Cells Vectors containing the ICE$_{rel}$-II encoding DNA sequence were used to drive the translation of the ICE$_{rel}$-II polypeptide in rabbit reticulocyte lysates, mammalian host cells, and in baculovirus infected insect cells. The experimental procedures were essentially those outlined in the manufacturers' instructions.

a) In vitro Transcription/Translation. pBluescript II SK+:ICE$_{rel}$-II plasmid DNA (with ICE$_{rel}$-II in the T7 orientation) was linearized by Bam HI digestion downstream of the ICE$_{rel}$-II insert. The linearized plasmid was purified and used as a template for run-off transcription using T7 RNA polymerase in the presence of m7G(5')ppp (5')G. The resulting capped ICE$_{rel}$-II transcripts were purified by lithium chloride precipitation and used to drive the translation of ICE$_{rel}$-II in nuclease-pretreated rabbit reticulocyte lysate in the presence of L-[$^{35}$S]methionine. The resulting translation mixtures contained radiolabelled ICE$_{rel}$-II protein which migrated on SDS/polyacrylamide gels with an apparent molecular mass of 45±2 kDa.

b) Expression in Mammalian Cells. The ICE$_{rel}$-II protein was expressed in mammalian host cells following transfection with either pcDNA I/Amp:ICE$_{rel}$-II (under control of the CMV promoter) or pSZ9016-1:ICE$_{rel}$-II (under control of the HIV LTR promoter). In the latter case (pSZ9016-1:ICE$_{rel}$-II), cells were co-transfected with the TAT expressing plasmid pSZ90161:TAT. For both ICE$_{rel}$-II expression plasmids, COS-7 cells were transfected using either DEAE-dextran or lipofection with Lipofectamine (BRL).

c) Expression in Insect Cells. The ICE$_{rel}$-II-containing baculovirus transfer vector pVL1393:T7 ICE$_{rel}$-II HA was used to produce recombinant baculovirus (*Autographa californica*) by in vivo homologous recombination. Epitope tagged ICE$_{rel}$-II was then expressed in Sf9 (*Spodoptera frugiperda*) insect cells grown in suspension culture following infection with the ICE$_{rel}$-II-containing recombinant baculovirus.

EXAMPLE 4

Cloning of ICE$_{rel}$-II for Expression of the ICE$_{rel}$-II Polypeptide In Other Host Cell Systems a) Cloning of ICE$_{rel}$-II cDNA into a bacterial expression vector. Recombinant ICE$_{rel}$-II is produced in a bacterium such as *E. coli* following the insertion of the optimal ICE$_{rel}$-II cDNA sequence into expression vectors designed to direct the expression of heterologous proteins. These vectors are constructed such that recombinant ICE$_{rel}$-II is synthesized alone or as a fusion protein for subsequent manipulation. Expression may be controlled such that recombinant ICE$_{rel}$-II is recovered as a soluble protein or within insoluble inclusion bodies. Vectors such as pBR322, pSKF, pUR, pATH, pGEX, pT7-5, pT7-6, pT7-7, pET, pIBI (IBI), pSP6/M7-19 (Gibco/BRL), pBluescript II (Stratagene), pTZ18R, pTZ19R (USB), pSE420 (Invitrogen) or the like are suitable for these purposes.

b) Cloning of ICE$_{rel}$-II cDNA into a yeast expression vector. Recombinant ICE$_{rel}$-II is produced in a yeast such as *Saccharomyces cerevisiae* following the insertion of the optimal ICE$_{rel}$-II cDNA cistron into expression vectors designed to direct the intracellular or extracellular expression of heterologous proteins. In the case of intracellular expression, vectors such as EmBLyex4 or the like are ligated to the ICE$_{rel}$-II cistron [Rinas, U. et al., *Biotechnology* 8: 543–545 (1990); Horowitz B. et al., *J. Biol. Chem.* 265: 4189–4192 (1989)]. For extracellular expression, the ICE$_{rel}$-II cistron is ligated into yeast expression vectors which fuse a secretion signal (a yeast or mammalian peptide) to the amino terminus of the ICE$_{rel}$-II protein [Jacobson, M. A., *Gene* 85: 511–516 (1989); Riett L. and Bellon N. Biochem. 28: 2941–2949 (1989)].

c) Cloning of ICE$_{rel}$-II cDNA into a viral expression vector. Recombinant ICE$_{rel}$-II is produced in mammalian host cells, such as HeLa S3 cells, after infection with vaccinia virus containing the ICE$_{rel}$-II cDNA sequence. To produce ICE$_{rel}$-II:vaccinia virus, the ICE$_{rel}$-II cDNA is first ligated into a transfer vector, such as pSC11, pTKgptF1 s, pMJ601 or other suitable vector, then transferred to vaccinia virus by homologous recombination. After plaque purification and virus amplification, ICE$_{rel}$-II:vaccinia virus is used to infect mammalian host cells and produce recombinant ICE$_{rel}$-II protein.

EXAMPLE 5

Process For The Production Of A Interleukin-1β Converting Enzyme-Related Cysteine Proteinase II Polypeptide Recombinant ICE$_{rel}$-II is produced by a) transforming a host cell with DNA encoding ICE$_{rel}$-II protein to produce a recombinant host cell;

b) culturing the recombinant host cell under conditions which allow the production of interleukin-1β converting enzyme-related cysteine proteinase II; and c) recovering the interleukin-1β converting enzyme-related cysteine proteinase II.

The recombinant interleukin-1β converting enzyme-related cysteine proteinase II is purified and characterized by standard methods.

EXAMPLE 6

Compounds that modulate interleukin-1β converting enzyme-related cysteine proteinase II activity may be detected by a variety of methods. A method of identifying compounds that affect interleukin-1β converting enzyme-related cysteine proteinase II comprises:

(a) mixing a test compound with a solution containing interleukin-1β converting enzyme-related cysteine proteinase II to form a mixture;

(b) measuring interleukin-1β converting enzyme-related cysteine proteinase II activity in the mixture; and (c) comparing the interleukin-1β converting enzyme-related cysteine proteinase II activity of the mixture to a standard.

Compounds that modulate interleukin-1β converting enzyme-related cysteine proteinase II activity may be formulated into pharmaceutical compositions. Such pharmaceutical compositions may be useful for treating diseases or conditions that are characterized by altered interleukin-1β converting enzyme-related cysteine proteinase II activity. Examples of diseases wherein the interleukin-1β converting enzyme-related cysteine proteinase II activity is increased include immune deficiency syndromes, pathogenic infections, cardiovascular and neurological injury, alopecia, aging, Parkinson's disease and Alzheimers disease. For these diseases, therapeutic treatment comprises treatment with compounds that decrease the interleukin-1β converting enzyme-related cysteine proteinase II activity. Examples of diseases wherein the interleukin-1β converting enzyme-related cysteine proteinase II activity is decreased include autoimmune diseases, leukemias, lymphomas and other cancers. For these diseases, therapeutic treatment comprises treatment with compounds that increase interleukin-1β converting enzyme-related cysteine proteinase II activity.

EXAMPLE 7

DNA which is structurally related to DNA encoding interleukin-1β converting enzyme-related cysteine proteinase II is detected with a probe. A suitable probe may be derived from DNA having all or a portion of the nucleotide sequence of FIG. 1, RNA encoded by DNA having all or a portion of the nucleotide sequence of FIG. 1, degenerate oligonucleotides derived from a portion of the amino acid sequence of FIG. 1 or an antibody directed against interleukin-1β converting enzyme-related cysteine proteinase II.

EXAMPLE 8

A kit useful for the detection and characterization of DNA or RNA encoding interleukin-1β converting enzyme-related cysteine proteinase II or interleukin-1β converting enzyme-related cysteine proteinase II is prepared by conventional methods. The kit may contain DNA encoding interleukin-1β converting enzyme-related cysteine proteinase II, recombinant interleukin-1μ converting enzyme-related cysteine proteinase II, RNA corresponding to the DNA encoding interleukin-1μ converting enzyme-related cysteine proteinase II or antibodies to interleukin-1β converting enzyme-related cysteine proteinase II. The kit may be used to characterize test samples, such as forensic samples or epidemiological samples.

EXAMPLE 9

Cloning of Other ICE$_{rel}$-II Genes Using Human ICE$_{rel}$-II Gene

The cross hybridization of the DNA representing portions of the ICE$_{rel}$-II gene to genomic DNA isolated from other organisms makes it possible to clone the homologous genes from the parent organisms. To do this, a genomic library from another primate such as a monkey is constructed from genomic DNA according to conventional methods. Using, for example, an EMBL vector, an EMBL genomic library is prepared, plated and screened by hybridization with a $^{32}$P-labeled DNA probe. Positive plaques are selected and subjected to additional screening until a purified cross-reacting plaque is selected. The DNA contained in the positive clone is further characterized by physical methods such as restriction mapping, Southern hybridization and DNA sequencing.

For example, purified nucleic acid encoding a functional interleukin-1β converting enzyme-related cysteine proteinase II from such an animal may be isolated by hybridizing an appropriate sample with nucleic acid encoding interleukin-1β converting enzyme-related cysteine proteinase II under low stringency conditions.

EXAMPLE 10

Use of Mutagenized ICE$_{rel}$-II DNA

DNA encoding ICE$_{rel}$-II is mutagenized using standard methods to produce an altered ICE$_{rel}$-II gene. Host cells are transformed with the altered ICE$_{rel}$-II to produce altered ICE$_{rel}$-II protein. The altered ICE$_{rel}$-II protein may be isolated, purified and used to characterize the function of ICE$_{rel}$-II protein.

What is claimed is:

1. An isolated and purified interleukin-1β converting enzyme-related cysteine proteinase II having the amino acid sequence of SEQ ID NO: 9.

2. A composition comprising the interleukin-1β converting enzyme-related cysteine proteinase II of claim 1.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 157 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGAAGGATG AGGTGGCCCT GCTGGCTGCT GTGACCCTGC TGGGCGTGCT GCTGCAGGCT      60

GGCTTCTCCC TGCAGGTGAT CTCTGCCCGG ATTGCCTTCC GGGTTCCATC TAAAAAAGGT     120

AGGTAGGTAA AAGAATTATA TTATCAAGTA TTTATTT                               157
```

(2) INFORMATION FOR SEQ ID NO:2:

(i) SEQUENCE CHARACTERISTICS:
      (A) LENGTH: 82 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
TGAGCAAGTT CAGCCTGGTT AAGTCTTTTT CCATCTAAAA AAGGTAGGTA GGTAAAAGAA       60

TTATATTATC AAGTATTTAT TT                                               82
```

(2) INFORMATION FOR SEQ ID NO:3:

(i) SEQUENCE CHARACTERISTICS:
      (A) LENGTH: 86 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

GGCTTATGAG TATTTCTTCC AGGGAGCAAA AACCCCATCT AAAAAAGGTA GGTAGGTAAA      60

AGAATTATAT TATCAAGTAT TTATTT      86

(2) INFORMATION FOR SEQ ID NO:4:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGGCCACTTC CAAGGATGCT GGACCATCTA AAAAAGGTAG GTAGGTAAAA GAATTATATT      60

ATCAAGTATT TATTT      75

(2) INFORMATION FOR SEQ ID NO:5:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CTGGAAGATG GTGTCATAAA GCAGCAAATC CATCTAAAAA AGGTAGGTAG GTAAAAGAAT      60

TATATTATCA AGTATTTATT T      81

(2) INFORMATION FOR SEQ ID NO:6:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAACTGGAAG GAAGAGGAAA TTCCATCTAA AAAAGGTAGG TAGGTAAAAG AATTATATTA      60

TCAAGTATTT ATTT      74

(2) INFORMATION FOR SEQ ID NO:7:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCATGCACAG TTCCGCAGAT TCCCTACCAT CTAAAAAAGG TAGGTAGGTA AAGAATTAT      60

ATTATCAAGT ATTTATTT      78

(2) INFORMATION FOR SEQ ID NO:8:

(i) SEQUENCE CHARACTERISTICS:

(A) LENGTH: 1299 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TTTCCAACGC TGTAAAAAAG GACAGAGGCT GTTCCCTATG GCAGAAGGCA ACCACAGAAA    60

AAAGCCACTT AAGGTGTTGG AATCCCTGGG CAAAGATTTC CTCACTGGTG TTTTGGATAA   120

CTTGGTGGAA CAAAATGTAC TGAACTGGAA GGAAGAGGAA AAAAGAAAT ATTACGATGC    180

TAAAACTGAA GACAAAGTTC GGGTCATGGC AGACTCTATG CAAGAGAAGC AACGTATGGC   240

AGGACAAATG CTTCTTCAAA CCTTTTTTAA CATAGACCAA ATATCCCCCA ATAAAAAAGC   300

TCATCCGAAT ATGGAGGCTG GACCACCTGA GTCAGGAGAA TCTACAGATG CCCTCAAGCT   360

TTGTCCTCAT GAAGAATTCC TGAGACTATG TAAAGAAAGA GCTGAAGAGA TCTATCCAAT   420

AAAGGAGAGA AACAACCGCA CACGCCTGGC TCTCATCATA TGCAATACAG AGTTTGACCA   480

TCTGCCTCCG AGGAATGGAG CTGACTTTGA CATCACAGGG ATGAAGGAGC TACTTGAGGG   540

TCTGGACTAT AGTGTAGATG TAGAAGAGAA TCTGACAGCC AGGGATATGG AGTCAGCGCT   600

GAGGGCATTT GCTACCAGAC CAGAGCACAA GTCCTCTGAC AGCACATTCT TGGTACTCAT   660

GTCTCATGGC ATCCTGGAGG GAATCTGCGG AACTGTGCAT GATGAGAAAA AACCAGATGT   720

GCTGCTTTAT GACACCATCT TCCAGATATT CAACAACCGC AACTGCCTCA GTCTGAAGGA   780

CAAACCCAAG GTCATCATTG TCCAGGCCTG CAGAGGTGCA AACCGTGGGG AACTGTGGGT   840

CAGAGACTCT CCAGCATCCT TGGAAGTGGC CTCTTCACAG TCATCTGAGA ACCTGGAGGA   900

AGATGCTGTT TACAAGACCC ACGTGGAGAA GGACTTCATT GCTTTCTGCT CTTCAACGCC   960

ACACAACGTG TCCTGGAGAG ACAGCACAAT GGGCTCTATC TTCATCACAC AACTCATCAC  1020

ATGCTTCCAG AAATATTCTT GGTGCTGCCA CCTAGAGGAA GTATTTCGGA AGGTACAGCA  1080

ATCATTTGAA ACTCCAAGGG CCAAAGCTCA AATGCCCACC ATAGAACGAC TGTCCATGAC  1140

AAGATATTTC TACCTCTTTC CTGGCAATTG AAAATGGAAG CCACAAGCAG CCCAGCCCTC  1200

CTTAATCAAC TTCAAGGAGC ACCTTCATTA GTACAGCTTG CATATTTAAC ATTTTGTATT  1260

TCAATAAAAG TGAAGACAAA CAAAAAAAAA AAAAAAAA                          1299

(2) INFORMATION FOR SEQ ID NO:9:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Xaa Xaa Xaa Xaa Met Ala Glu Gly Asn His Arg Lys Lys Pro Leu Lys
 1               5                  10                  15

Val Leu Glu Ser Leu Gly Lys Asp Phe Leu Thr Gly Val Leu Asp Asn
                20                  25                  30

Leu Val Glu Gln Asn Val Leu Asn Trp Lys Glu Glu Lys Lys Lys
         35                  40                  45

Tyr Tyr Asp Ala Lys Thr Glu Asp Lys Val Arg Val Met Ala Asp Ser
         50                  55                  60

Met Gln Glu Lys Gln Arg Met Ala Gly Gln Met Leu Leu Gln Thr Phe

-continued

```
 65                      70                      75                      80
Phe Asn Ile Asp Gln Ile Ser Pro Asn Lys Lys Ala His Pro Asn Met
                85                      90                      95
Glu Ala Gly Pro Pro Glu Ser Gly Glu Ser Thr Asp Ala Leu Lys Leu
               100                     105                     110
Cys Pro His Glu Glu Phe Leu Arg Leu Cys Lys Glu Arg Ala Glu Glu
               115                     120                     125
Ile Tyr Pro Ile Lys Glu Arg Asn Asn Arg Thr Arg Leu Ala Leu Ile
               130                     135                     140
Ile Cys Asn Thr Glu Phe Asp His Leu Pro Pro Arg Asn Gly Ala Asp
145                     150                     155                     160
Phe Asp Ile Thr Gly Met Lys Glu Leu Leu Glu Gly Leu Asp Tyr Ser
               165                     170                     175
Val Asp Val Glu Glu Asn Leu Thr Ala Arg Asp Met Glu Ser Ala Leu
               180                     185                     190
Arg Ala Phe Ala Thr Arg Pro Glu His Lys Ser Ser Asp Ser Thr Phe
               195                     200                     205
Leu Val Leu Met Ser His Gly Ile Leu Glu Gly Ile Cys Gly Thr Val
               210                     215                     220
His Asp Glu Lys Lys Pro Asp Val Leu Leu Tyr Asp Thr Ile Phe Gln
225                     230                     235                     240
Ile Phe Asn Asn Arg Asn Cys Leu Ser Leu Lys Asp Lys Pro Lys Val
               245                     250                     255
Ile Ile Val Gln Ala Cys Arg Gly Ala Asn Arg Gly Glu Leu Trp Val
               260                     265                     270
Arg Asp Ser Pro Ala Ser Leu Glu Val Ala Ser Ser Gln Ser Ser Glu
               275                     280                     285
Asn Leu Glu Glu Asp Ala Val Tyr Lys Thr His Val Glu Lys Asp Phe
               290                     295                     300
Ile Ala Phe Cys Ser Ser Thr Pro His Asn Val Ser Trp Arg Asp Ser
305                     310                     315                     320
Thr Met Gly Ser Ile Phe Ile Thr Gln Leu Ile Thr Cys Phe Gln Lys
               325                     330                     335
Tyr Ser Trp Cys Cys His Leu Glu Glu Val Phe Arg Lys Val Gln Gln
               340                     345                     350
Ser Phe Glu Thr Pro Arg Ala Lys Ala Gln Met Pro Thr Ile Glu Arg
               355                     360                     365
Leu Ser Met Thr Arg Tyr Phe Tyr Leu
370                     375
```